United States Patent
Langley

(10) Patent No.: US 11,897,833 B2
(45) Date of Patent: *Feb. 13, 2024

(54) REMOVING ORGANIC ACIDS IN MONOETHYLENE GLYCOL RECOVERY

(71) Applicant: Cameron International Corporation, Houston, TX (US)

(72) Inventor: Steven Langley, Croydon (GB)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 9 days.

This patent is subject to a terminal disclaimer.

(21) Appl. No.: 17/658,739

(22) Filed: Apr. 11, 2022

(65) Prior Publication Data

US 2022/0380281 A1    Dec. 1, 2022

Related U.S. Application Data

(63) Continuation of application No. 16/570,799, filed on Sep. 13, 2019, now Pat. No. 11,325,878.

(51) Int. Cl.
| | |
|---|---|
| *C07C 29/80* | (2006.01) |
| *C07C 29/88* | (2006.01) |
| *C07C 29/84* | (2006.01) |
| *B01D 3/32* | (2006.01) |
| *B01D 3/14* | (2006.01) |
| *B01D 1/00* | (2006.01) |
| *B01D 3/06* | (2006.01) |
| *C07C 31/20* | (2006.01) |
| *B01D 3/00* | (2006.01) |

(52) U.S. Cl.
CPC ............ *C07C 29/80* (2013.01); *B01D 1/0082* (2013.01); *B01D 3/06* (2013.01); *B01D 3/143* (2013.01); *B01D 3/322* (2013.01); *C07C 29/84* (2013.01); *C07C 29/88* (2013.01); *B01D 3/009* (2013.01); *C07C 31/202* (2013.01)

(58) Field of Classification Search
None
See application file for complete search history.

(56) References Cited

U.S. PATENT DOCUMENTS

| | | | |
|---|---|---|---|
| 6,525,229 | B2 | 2/2003 | Baars et al. |
| 9,732,019 | B1 | 8/2017 | Langley et al. |
| 11,325,878 | B2 | 5/2022 | Langley |
| 2015/0119609 | A1 | 4/2015 | Deshmukh |

(Continued)

FOREIGN PATENT DOCUMENTS

| | | | |
|---|---|---|---|
| EP | 2860168 A1 | 4/2015 | |
| WO | WO-2017052377 A1 * | 3/2017 | ............ C07C 29/78 |

OTHER PUBLICATIONS

Brustad, S. et al. "Hydrate Prevention using MEG instead of MeOH: Impact of experience from major Norwegian developments on technology selection for injection and recovery of MEG" May 2005, pp. 1-10 (Year: 2005).*

(Continued)

*Primary Examiner* — Medhanit W Bahta
(74) *Attorney, Agent, or Firm* — Jeffrey D. Frantz

(57) ABSTRACT

Embodiments described herein provide a method, comprising reducing pH of a glycol vaporization separator purge stream to form an acid stream; distilling the acid stream to form an overhead stream and a bottoms stream; and recycling the bottoms stream to the vaporization separator.

20 Claims, 5 Drawing Sheets

(56) References Cited

U.S. PATENT DOCUMENTS

2019/0233356 A1     8/2019   Messenger
2019/0241493 A1     8/2019   Phelps et al.

OTHER PUBLICATIONS

Soames, A. et al "Operation of a MEG pilot regeneration system for organic and Alkalinity removal during MDEA to FFCI switchover" Journal of Petroleum Science and Engineering 169 (2018) 1-14.
Bikkina, C. et al "Development of MEG Regeneration Unit Compatible Corrosion Inhibitor for Wet Gas Systems" Oct. 2012, pp. 1-11.
International Search Report and Written Opinion of PCT Application No. PCT/US2020/050229 dated Dec. 23, 2020 (13 pages).
Zaboon, S. et al., Recovery of mono-ethylene glycol by distillation and the impact of dissolved salts evaluated through simulation of field data, Journal of Natural Gas Science and Engineering, 2017, vol. 44, pp. 214-232.
Teixeira, A. M. et al., Exergy analysis of monoethylene glycol recovery processes for hydrate inhibition in offshore natural gas fields, Journal of Natural Gas Science and Engineering, 2016, vol. 35, pp. 798-813.
Lehmann, M. et al., Corrosion inhibitor and oxygen scavenger for use as MEG additives in the inhibition of wet gas pipelines, Offshore technology conference, 2014, pp. 1-20.

\* cited by examiner

REMOVING ORGANIC ACIDS IN MONOETHYLENE GLYCOL RECOVERY

CROSS-REFERENCE TO RELATED APPLICATION

This application is a Continuation of U.S. Non-Provisional application Ser. No. 16/570,799, filed on Sep. 13, 2019, which is hereby incorporated by reference in its entirety for all purposes.

FIELD

Embodiments of the present invention generally relate to gas hydrates processing in hydrocarbon extraction. Specifically, methods and apparatus for recovering used glycol processing aids are described.

BACKGROUND

Glycol processing aids are used in the oil and gas industry to suppress formation of natural gas hydrates. Under certain circumstances commonly present in gas processing, methane can complex with water to form hydrate crystals that can foul equipment and make processing and transportation of natural gas streams difficult and costly. Water in natural gas can also freeze, and can carry acids to form corrosive liquids that can compromise equipment. Glycol processing aids, for example monoethylene glycol, are commonly used in the oil and gas industry to sequester water in natural gas streams. Such processing aids are expensive, and the large volumes of natural gas produced require large volumes of glycol processing aids. For this reason, the glycol processing aids are recovered, purified, and recycled.

Fluid from natural gas streams containing glycol processing aids is routed to a glycol recovery unit. The glycol is typically vaporized in a vaporization apparatus to separate the glycol from contaminants and impurities from the natural gas stream. In a typical process, the fluid is pumped through a heater in a recycle loop to add heat. Glycol and some water are vaporized in one or many passes through the apparatus. The fluid portion in the apparatus is typically pumped through a heater to add heat and returned to the apparatus. As the fluid is pumped around through the heater, and as glycol and water are removed, concentration of impurities and contaminants grows in the fluid. In a conventional process, the fluid is periodically removed from the vaporization apparatus to address the impurity buildup.

A primary impurity that builds up in the fluid and drives the periodic removal is organic acid salt, such as sodium acetate. This salt increases the viscosity of the fluid pumped through the heater adversely impacting operation of the vaporization apparatus. Conventional methods of counteracting the buildup of sodium acetate involve discarding the fluid from the vaporization apparatus periodically, which also discards large amounts of valuable glycol processing aid. There is a need in the industry for methods and apparatus to remove organic acid salts from glycol recovery facilities while minimizing loss of glycol.

SUMMARY

Embodiments described herein provide a method, comprising reducing pH of a glycol vaporization separator purge stream to form an acid stream; distilling the acid stream to form an overhead stream and a bottoms stream; and recycling the bottoms stream to the vaporization separator.

Other embodiments described herein provide a method, comprising detecting a physical property of a pumparound stream of a glycol vaporization separator; comparing the physical property one or more threshold values; withdrawing a purge stream from the pumparound stream if the physical property reaches a threshold value; reducing pH of the purge stream to form an acid stream; distilling the acid stream to form an overhead stream and a bottoms stream; and recycling the bottoms stream to the glycol vaporization separator.

Other embodiments described herein provide a method, comprising withdrawing a purge stream from a liquid volume of a glycol vaporization separator based on a physical property of the liquid volume; mixing an aqueous acid with the purge stream to form an acid stream at a rate of the aqueous acid that is based on a pH of the acid stream; providing the acid stream to a packed distillation column at a location below a packing inside the packed distillation column; distilling the acid stream to form an overhead stream and a bottoms stream; and recycling the bottoms stream to the glycol vaporization separator.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
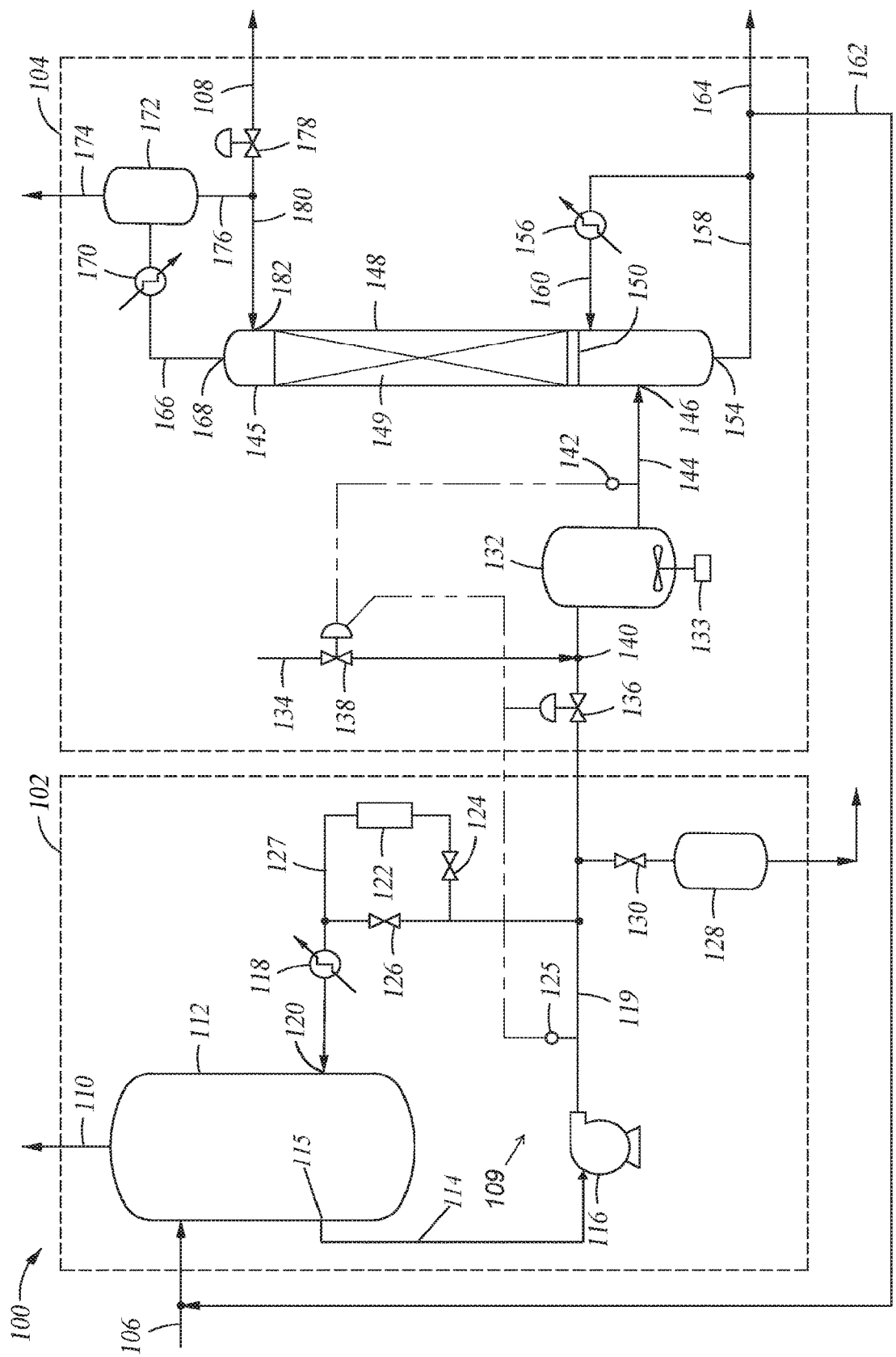
FIG. 1 is a process diagram illustrating a process according to one embodiment.

FIG. 1 is a process diagram of a glycol recovery process 100 according to one embodiment. The glycol recovery process 100 includes a glycol separation section 102 and an acid recovery section 104. The glycol separation section 102 includes a glycol vaporization separator vessel 112 with a feed 106, a draw point 115, and an overhead 110. Glycol is vaporized, along with any co-boiling materials such as water, in the vaporization vessel 112. The vaporized glycol exits through the overhead 110.

A fluid mixture is withdrawn through a fluid draw 114 at the draw point 115, which may be at a low point or side draw of the vaporization vessel 112. The vessel 112 may be a flash vessel that vaporizes glycol from a glycol containing stream, with a salt separation zone in a lower portion of the vessel 112 that separates salts from the glycol containing liquid. In such cases, the fluid mixture may be withdrawn from a side draw of the vessel 112. The fluid mixture typically contains glycol and water, along with some solids. The fluid draw 114 is routed to a pump 116 that drives a pumparound loop 109. The pump discharge is routed through a pumparound line 119 to a heater 118, and the heated fluid mixture is routed back to the vessel 112 at a recycle point 120. A solids removal unit 122 may be provided in the pumparound loop 109 to remove solids, such as salt crystals, from the fluid mixture. A pumparound block valve 126 may be provided in the pumparound line 119 to route the fluid mixture through a divert line 127 to the solids removal unit 122. A divert block valve 124 can be used, along with the pumparound block valve 126, to control routing the fluid mixture through the solids removal unit 122, or directly to the vaporization vessel 112. The solids removal unit may be any convenient type of solids removal unit, including a filter unit, a centrifuge unit, a hydrocyclone unit, or any other suitable solids removal unit.

The vaporization vessel 112 vaporizes volatile components of the feed 106, chiefly glycol and water. The material flowing through the feed line 106 is usually a rich glycol stream sourced from an oil and gas recovery process where an initial separation of glycol containing fluid from gas and liquid hydrocarbon has been performed. Commonly the glycol recovery process 100 is recovering monoethylene glycol (MEG), but other glycol recovery processes can benefit from embodiments described herein. The vessel 112 may be operated under vacuum to reduce vaporization temperature and minimize thermal degradation of glycols in the vessel 112. A portion of the fluid mixture in the pumparound line 119 may be routed to a disposal vessel 128 through disposal valve 130.

Another portion of the fluid mixture, or in some cases all the fluid mixture, is routed to the acid recovery section 104. The acid recovery section includes an acid treatment vessel 132. Flow of the fluid mixture to the acid treatment vessel 132 is controlled by control valve 136. A sensor 125, for example a density or viscosity sensor, can be coupled to the pumparound line 119 between the discharge of the pump 116 and the heater 118 to monitor buildup of salts in the fluid in the vessel 112. When the sensor 125 detects a physical property such as density reaching a first threshold, the control valve 136 can be opened to flow a portion of the fluid to the vessel 132. When the detected property reaches a second threshold, the control valve 136 can be closed to stop acid treatment. In the case of a density measurement, the first threshold may be an upper threshold indicating that organic acid salts need treatment, and the second threshold may be a lower threshold indicating that organic acid salts have reached a low level that does not require treatment. Thus, fluid can flow continuously or intermittently from the glycol separation section 102 to the acid treatment vessel 132. Alternatively, the decision on treatment could be made by operator sampling. If a sample taken by an operator and subjected to appropriate analysis shows the need for treatment, the control valve 136 can be opened to begin treatment, and vice versa.

Acid treatment is added through acid treatment line 134 to mixing point 140 prior to the fluid mixture entering the acid treatment vessel 132. Flow rate of the acid treatment is controlled by control valve 138. The acid treatment lowers pH of the fluid mixture transforming at least some organic acid salts into volatile organic acids. An acid stream is withdrawn through an effluent line 144 of the vessel 132. A pH sensor 142 is coupled to the effluent line 144 to monitor pH of the effluent, and can be operatively coupled to the control valve 138 to control addition of acid treatment based on pH of the effluent. Additionally or alternately, flow of acid treatment can be controlled according to flow rate of fluid through the control valve 136, for example under ratio control.

Conversion of organic acid salts into organic acids is influenced by pH, which can be used to control the process. Lower pH increases conversion. Any acidic pH (below 7.0) will convert at least some organic acid salts to organic acids, with pH at 4.0 or below converting most organic acid salts to acids. Thus, pH can be used to control conversion of organic acid salts to volatile acids. A pH target can be defined, and the pH sensor 142 used to control addition of acid treatment to reach the pH target. The pH target can be lowered to increase conversion of organic acid salts to volatile acids or raised to reduce conversion. Flow rate of fluid from the glycol separation section 102 to the acid treatment vessel 132 can be used together with pH target to control overall treatment of organic acid salts.

To aid mixing of acid treatment and equalization of pH throughout the acid treatment vessel 132, a mixer 133 may be coupled to the acid treatment vessel 132. High shear mixers featuring agitators, which may be single or multiple and may be counter-rotating, or pumparound loops with static mixers and/or jet mixers, can be used to maximize mixing in the acid treatment vessel 132.

The acid recovery section 104 also includes a distillation column 148 downstream of the acid treatment vessel 132. A low pH fluid flows through the effluent line 144 to the distillation column 148. The distillation column 148 removes the volatile organic acids from the fluid mixture. A separation structure 149 inside the distillation column 148 provides surface area for vapor-liquid equilibrium. The separation structure 149 may be a packing material or a plurality of trays. The effluent line 144 of the acid treatment vessel 132 is coupled to a feed point 146 in the lower portion of the distillation column 148 to deliver the acid stream from the acid treatment vessel 132 to the distillation column 148. The acid stream descends to the bottom of the distillation column 148, mixing with bottoms fluid in the bottom of the distillation column 148. The bottoms fluid is removed at a bottom point 154 of the distillation column 148 into a bottoms line 158. A fluid level may be maintained in the bottom portion of the distillation column 148. The bottoms fluid is circulated through a heater 156 and through a return line 160 to the distillation column 148. The return line 160 delivers the heated bottoms fluid to the distillation column 148 below a lower tray 150, which may be a chimney tray, located in the distillation column 148 above the feed point 146 of the distillation column 148. Thus, the return fluid may be delivered to the distillation column 148 between the feed point 146 and the lower tray 150 or below the feed point 146. The lower tray 150 may be omitted in some embodiments. A portion, which may be a majority, of the bottoms fluid is returned to the vaporization section 102 through a recycle line 162, here joined with the feed line 106 to the vaporization vessel 112. A portion of the bottoms fluid may be purged from the bottoms line 158, as well, through bottoms purge line 164.

Volatile organic acids, such as acetic acid, are taken overhead in the distillation column 148. Vapor concentrated in organic acids is withdrawn from vapor withdrawal point 168 into overhead line 166. The vapor is cooled in cooler 170, which may partially condense the vapor. An overhead vessel 172 collects any condensate, which exits through condensate line 176. Some condensate may be returned to an upper portion of the distillation column 148 as reflux through reflux line 180 to reflux point 182, while some can be taken as an acid overhead 108. Liquid level in the overhead drum can be controlled using control valve 178. Uncondensable vapor is removed from the overhead vessel 172 through vapor line 174.

Any acid can be used to lower the pH of the fluid at the mixing location 140. One acid that is convenient for this process is hydrogen chloride (HCl), since the reaction product is primarily sodium chloride which can be easily removed. However, other acids can also be used. Acid is recycled with the bottoms fluid to the vaporizer 102, so acid addition at the mixing location 140 compensates for acid loss in the disposal vessel 128, the bottoms purge line 164, and neutralization with acid-reactive species incoming via the feed line 106. The pH sensor 142 allows for acid addition to be controlled to target a desired pH for the feed to the distillation column 148.

Figure 2:
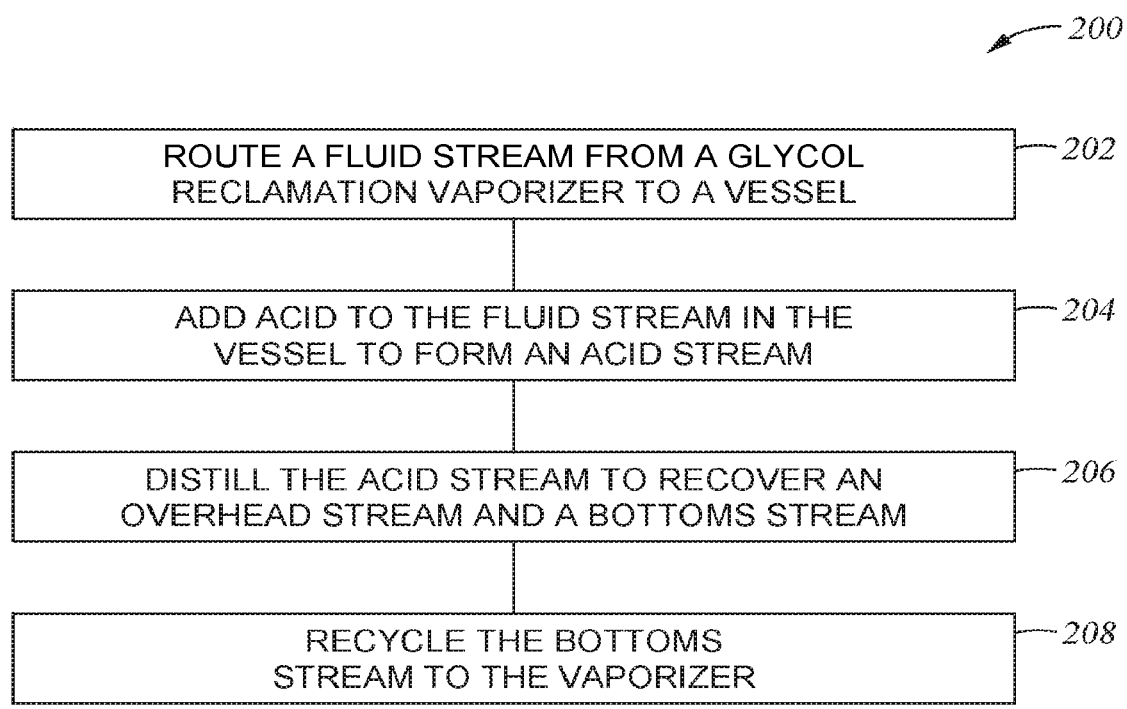
FIG. 2 is a flow diagram summarizing a method according to one embodiment.

FIG. 2 is a flow diagram summarizing a method 200 according to one embodiment. The method 200 is a method of recovering glycol from a wellhead stream. At 202, fluid stream, which may be a rich glycol stream, from a glycol reclamation vaporizer is routed to a vessel. The vaporizer receives the rich glycol feed stream into a volume of hot glycol containing fluid that heats the feed stream to a temperature that vaporizes glycol and water. The feed stream commonly contains water, various salts, and some trace hydrocarbon, along with glycol.

The hot glycol containing fluid in the vaporizer is typically maintained at a vaporization temperature to vaporize the incoming rich glycol. A stream of the hot glycol containing fluid is withdrawn from the vessel and passed through a heater to maintain the temperature of the hot glycol containing fluid. Since the salts do not vaporize in the vaporizer, the salts can build up in the hot glycol containing fluid, increasing the viscosity thereof and generally complicating the task of pumping and heating the hot glycol containing fluid. Some salts crystallize at fairly low loadings and can be separated, but other salts, such as some organic acid salts, are more soluble in glycols. Acetates, for example, such as sodium acetate have some solubility in glycols that complicates their removal from glycol containing fluids. A treatment portion of the hot glycol containing fluid is thus withdrawn from the vaporization vessel to another vessel.

At 204, acid is added to the vessel containing the treatment portion to form an acid stream. The acid lowers the pH of the treatment portion withdrawn from the vaporization vessel, converting organic acid salts to acid form. Sodium acetate salts, for example, are converted to acetic acid and a salt more stable at lower pH. Any pH below 7.0, for example 4.0 or 4.5, or lower pH such as 2.0 or 2.5, will convert at least some organic acid salts to organic acids, with lower pH resulting in higher conversion. Thus, pH can be used to control conversion of organic acid salts to organic acids.

The acid may be any acid stronger than the conjugate acids of the organic acid salts. Acetic acid, for example, has a pKa of about 4.75, so acids with lower pKa can be used to reconstitute acetic acid from an acetate salt. For many oil and gas processing applications, chloride salts are present from formation water, so HCl can be a convenient choice. Other acids can also be used.

The acid is mixed with the fluid in the vessel, which provides residence time for the reaction in a well-mixed vessel. After the acidification process, a quantity of organic acid salts in the treatment portion has become organic acid in the acid stream. At 206, the acid stream is distilled to recover an overhead stream and a bottoms stream. The acid stream is provided to a distillation column that separates the more volatile organic acids, such as acetic acid, from the less volatile glycol. The distillation column is reboiled to add heat for vaporizing water and organic acids, and may be refluxed to reduce glycol losses in the column overhead. The distillation column typically has an internal separation structure that may be an acid resistant packing or tray structure.

In the event an acid resistant packing is used, the acid stream may be provided to the distillation column at a location below the packing to avoid fouling the packing material. In one example, the acid stream is provided to the distillation column at a feed point of the distillation column located just below the packing. The acid stream enters hot descending fluid in the distillation column, where some light material is vaporized and rises toward the packing material. The remaining fluid descends to the bottom of the column and is withdrawn to reboiler. Alternately, the acid stream can be added directly to the reboiler. For a distillation column operated at near atmospheric pressure, the fluid is heated in the reboiler to a temperature between about 250° F. and about 300° F., for example about 280° F. The column can be operated at a lower temperature if pressure is reduced. Operating at lower temperature reduces decomposition rate of some glycols. In any event, the reboiled stream is returned to the distillation column. In some cases, the reboiled bottoms stream is returned to the distillation column at a location above the feed location. A return tray may be provided between the feed tray and the packing to receive the return stream. Alternately, the return tray can be between the feed tray and the bottom of the column. In some cases the feed stream is provided to the distillation column near the bottom of the packing material, and the reboiled stream is returned to the column below the feed location, to minimize concentration of organic acids in the bottoms stream.

As mentioned briefly above, vapor rises in the distillation column and is removed overhead. The vapor can be passed to a cooler, which can be operated to at least partially condense the vapor. The vapor is concentrated in water and organic acids, potentially with other more volatile species. Any condensed liquids can be collected in an accumulator, and a portion of the condensate can be returned to the distillation column as reflux, which may be subcooled, for example by passing the reflux through a subcooler before returning to the distillation column. Subcooling the reflux can be used to increase the effective column reflux ratio where the column contains some organic acids with boiling points near the glycol component in the column, potentially at the expense of slightly increased concentration of organic acids in the bottom stream of the column. The overhead not returned to the distillation column as reflux is then passed to further processing or disposal.

At 208, a portion of the bottoms stream from the distillation column is recycled to the vaporizer to return the glycol to the vaporization process. The bottoms stream may be returned directly to the liquid volume of the vaporizer or into the suction of the pumparound pump. The temperature of the bottoms stream returned to the vaporizer is higher than that of the hot glycol containing fluid in the vaporizer, in some cases. Returning the bottoms stream to the vaporizer at a location upstream of the pumparound heater, for example, can reduce the heating load of the vaporization heater, effectively integrating the reboiler heat with the vaporization process.

Figure 3:
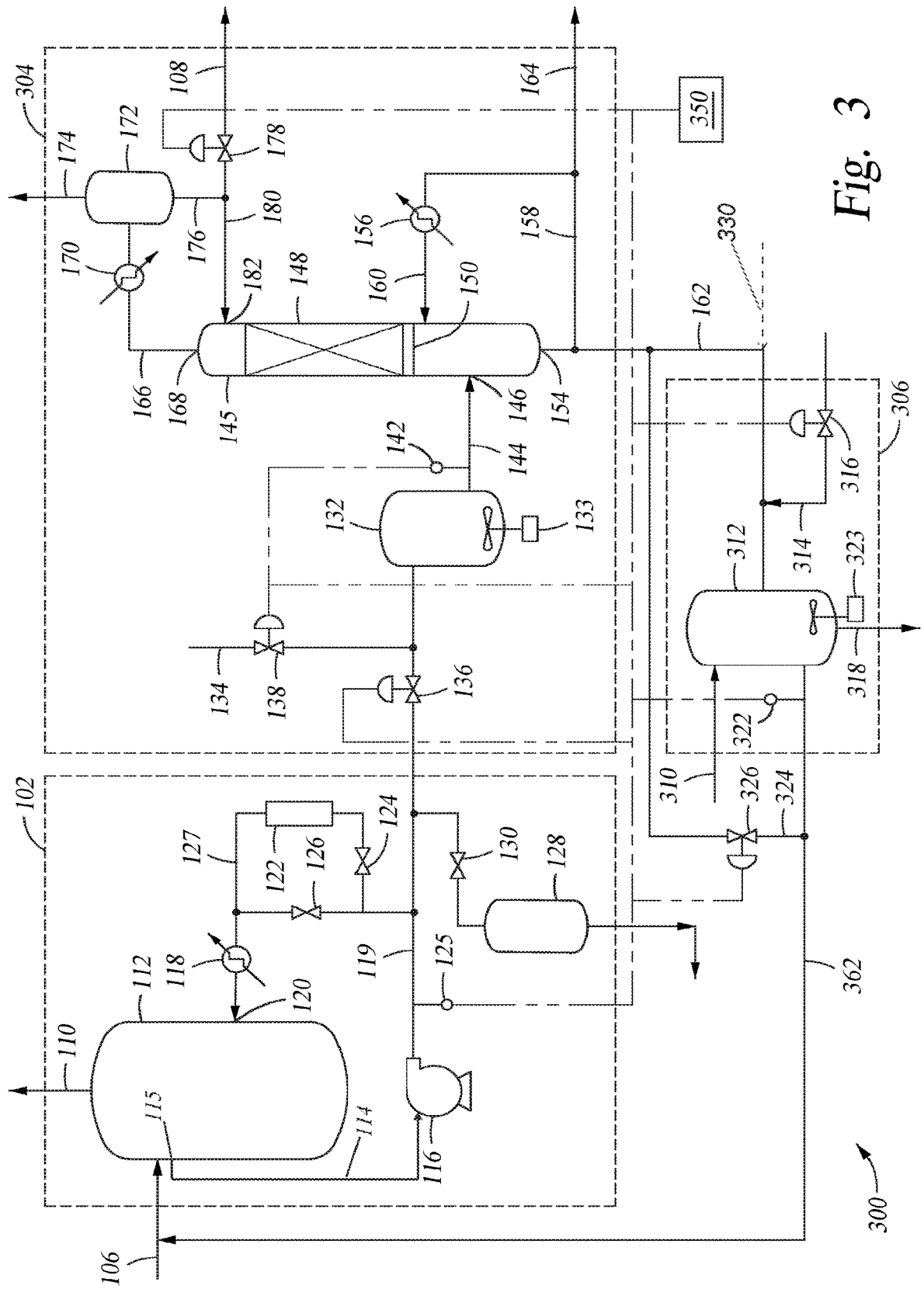
FIG. 3 is a process diagram illustrating a process according to another embodiment.

FIG. 3 is a process diagram illustrating a process 300 according to another embodiment. The process 300 is similar to the process 100 of FIG. 1, with the addition of a divalent removal section 306. Here, material from the bottom of the distillation column 148 recycled through recycle line 162 is routed to the divalent removal section 306. A divalent removal treatment is added to the recycled fluid through divalent removal treatment line 314. Flow rate of the divalent removal treatment is controlled by divalent removal treatment control valve 316, which is operatively coupled to the controller 350. The divalent removal treatment increases pH of the fluid in the recycle line 162 to precipitate solids containing divalent species. The mixture is provided to a divalent removal vessel 312 that provides residence time for reaction, settling capacity for solids removal, and mixing to increase divalent removal.

The divalent removal treatment is an aqueous solution of inorganic base, such as sodium or potassium carbonate or hydroxide, or mixtures thereof. The pH of the aqueous phase can be increased above about 8 to precipitate divalent ions as salts. Calcium, and other divalent ions in solution in the distillation bottoms fluid, if any, reacts with the divalent removal treatment and precipitates. Solids collect in the divalent removal vessel for disposal. A mixer 323, such as any of the mixers described above, can be provided to mix the ingredients thoroughly.

The divalent removal section 306 converts divalent species to solids. A solids containing stream 318 is removed from a low portion of the divalent removal vessel 312. Alternately, or additionally, the fluid in the divalent removal vessel 312 can be filtered, for example by using a pumparound loop with filter. The pumparound loop can also have mixing components such as static mixers and jet mixers.

A recycle line 362 is coupled to the divalent treatment vessel 312 to bring recycle fluid from the distillation bottoms, potentially depleted of divalent species, back to the vaporization section 102. A pH sensor 322 can be coupled to the recycle line 362 to control addition of reagent in the divalent removal treatment line 314. The pH sensor can be operatively coupled to the divalent removal treatment control valve 316 and/or to the controller 350.

An additive addition line 310 may be provided and coupled to the divalent removal treatment vessel 312 to allow additives, such as surfactants, buffers, density and/or viscosity modifiers, flocculants, and the like, to be added to the divalent removal treatment vessel 312 to aid in mixing and/or other processing in the divalent removal treatment vessel. Additional water can also be added through the additive addition line 310 to dilute the mixture for better mixing and to provide more extractive volume for removing divalent species.

An alternative, in the process 300 of FIG. 3, is to add the feed material of the feed stream 106 at the divalent treatment vessel. Thus, a feed line 330 may be coupled to the recycle line 162 to provide rich glycol feed from the oil and gas recovery process to the glycol recovery process 300 at the recycle line 162, leading to the divalent removal vessel. When such measures are taken, addition of divalent treatment at 314 is controlled using divalent treatment control valve 316 commensurate with the total flow of divalent species into the divalent treatment vessel 312. As noted above, the pH sensor 322 can be used to determine how flow rate of divalent treatment should be adjusted. The flow of rich glycol feed can also be split between the feed line 106 and the feed line 330.

A divalent treatment bypass 324 can be provided connecting the distillation bottoms line 162 to the recycle return line 362. The bypass 324 can have a control valve 326 that controls flow through the bypass 324 and through the divalent treatment vessel 312. The divalent treatment bypass 324 provides the capability to skip divalent treatment in the process 300 for a desired period of time, or to split flow in the recycle stream 162 to flow a first portion of the recycle stream 162 to the divalent removal vessel 312 and a second portion directly to the recycle return line 362, and to the vaporization vessel 112, without divalent treatment.

Figure 4:
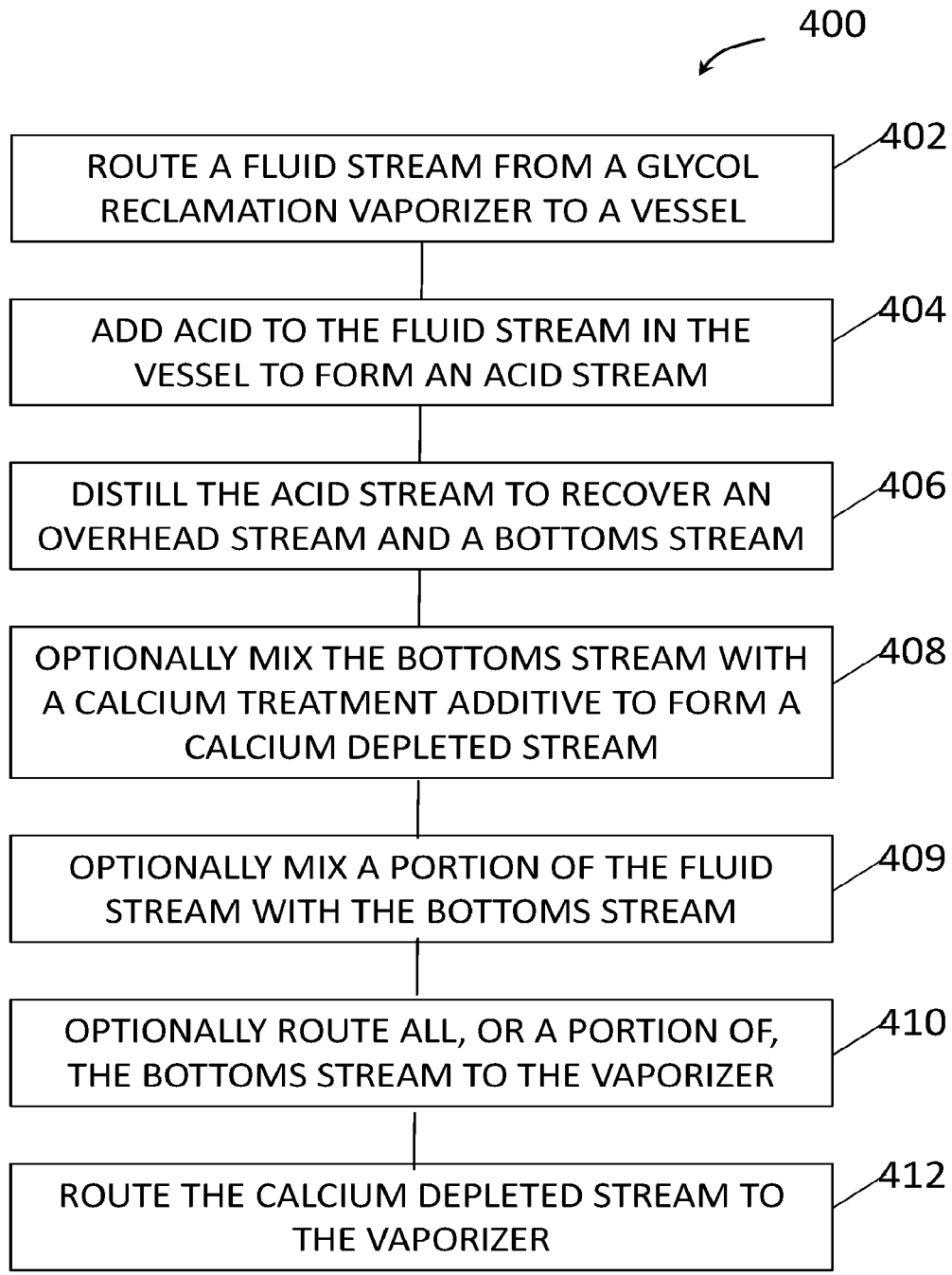
FIG. 4 is a flow diagram summarizing a method according to another embodiment.

FIG. 4 is a flow diagram summarizing a method 400 according to another embodiment. The method 400 is similar to the method 200 in many respects, with the additional aspect here that a divalent treatment can be included. At 402, a fluid stream from a glycol reclamation vaporizer is routed to a vessel, similar to operation 202 above. At 404, acid is added to the vessel in a manner similar to operation 204 above. At 406, the mixture is distilled to recover an overhead stream containing organic acids and a bottoms stream, similar to operation 206. At 408, the bottoms stream is optionally mixed with a divalent treatment additive to form a divalent depleted stream. The additive is a reagent that causes calcium, and other divalent species, to be separated from the bottoms stream, usually as a solid. The divalent treatment additive may be a caustic reagent that raises the pH of the bottoms stream to precipitate divalent species as salts. Reagents like sodium and potassium hydroxide, or other metal hydroxides, ammonium hydroxide, metal carbonates such as sodium and potassium carbonate, sodium borate (borax), sodium phosphate, and the like, can be used.

At 409, the bottoms stream, or a portion thereof, can optionally be directly mixed with the fluid stream from the vaporizer to assist in raising the pH stream for divalent removal. A controller can control the amount of the fluid stream mixed with the bottoms stream or provided to the acid treatment based, for example, on density or viscosity of the fluid stream obtained from the vaporizer. In one embodiment, if a property of the fluid stream reaches a first threshold, no fluid stream is withdrawn from the vaporizer. If the fluid stream property is between the first threshold and a second threshold, a first portion of the fluid stream can be routed to acid treatment and a second portion to divalent removal, depending on proximity of the fluid stream property to the second threshold. If the fluid stream property reaches the second threshold, no fluid stream is routed to divalent removal. Other control schemes can also be used.

Optionally, at 410, all, or a portion of, the bottoms stream may be routed to the glycol reclamation vaporizer, bypassing the divalent treatment. At 412, the divalent depleted stream is routed to the glycol reclamation vaporizer, returning the portions of the fluid originally withdrawn from the vaporizer and not removed by the acid treatment and optional divalent removal treatment. The portion returned is thus depleted of organic acid salts and, optionally, divalent species.

Figure 5:
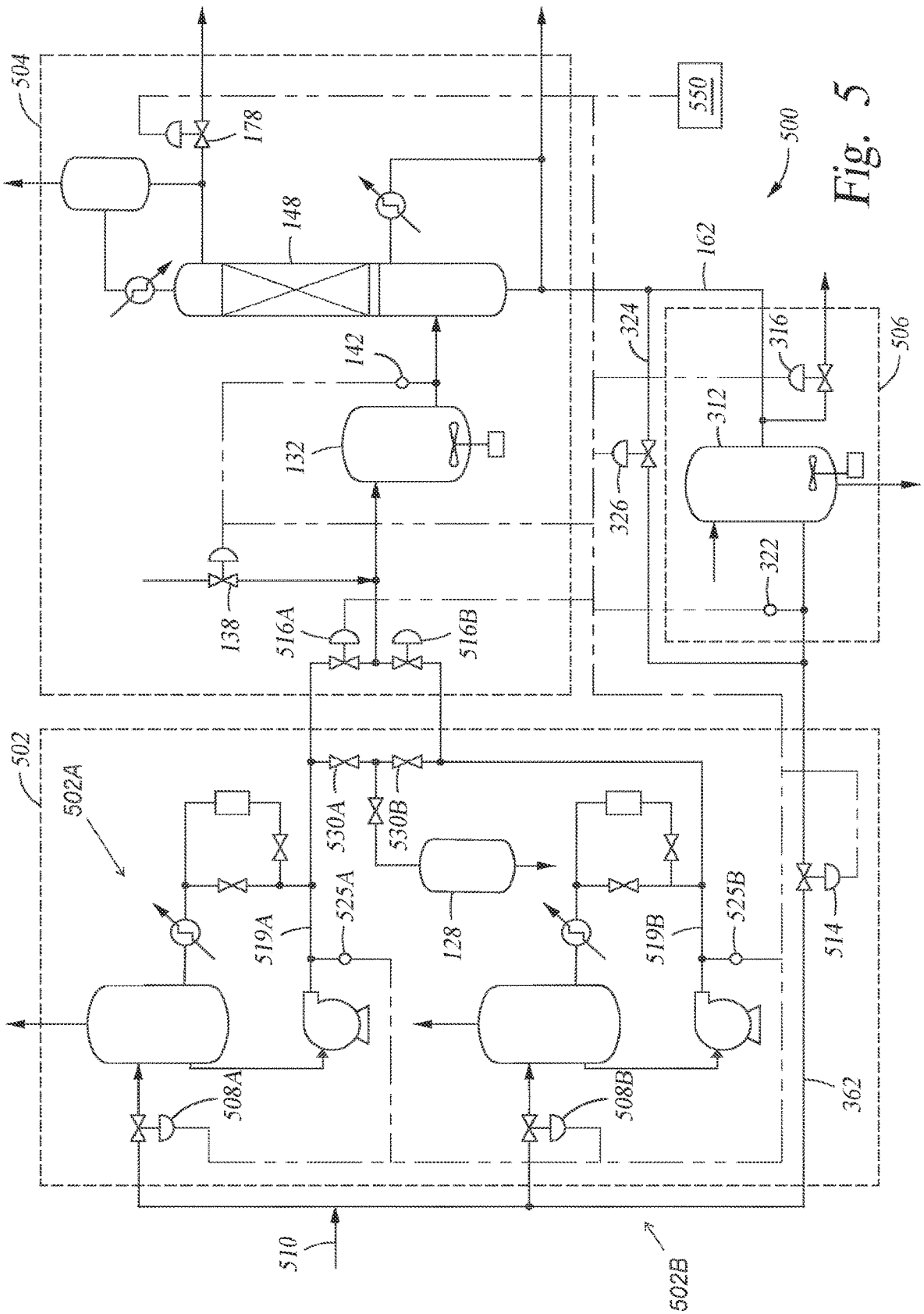
FIG. 5 is a process diagram illustrating a process according to another embodiment.

FIG. 5 is a process diagram illustrating a process 500 according to another embodiment. The process 500 is similar to the process 300, and can be used to practice the methods 200 and 400. The process 500 is different from the process 300 in that the process 500 has a glycol separation section 502 with multiple glycol reclamation vaporizers. In the version of FIG. 5, the process 500 has two vaporizers, a first vaporizer 502A and a second vaporizer 502B, which are like the vaporizer 102 of FIGS. 1 and 3. Each maintains a hot glycol volume in a liquid zone. A rich glycol feed stream 510 is shown divided between the two vaporizers 502A and 502B, but a dedicated feed stream could be provided for each vaporizer. Each vaporizer has a pump and a respective first and second pumparound line 519A and 519B. It should be noted that any or all of the glycol vaporization separators described herein can be flash separators, in which glycol and water are flashed in a hot volume of glycol containing liquid.

A portion of the stream in each of the pumparound lines 519A and 519B can be routed to the acid treatment vessel 132 using respective purge feed control valves 516A and 516B. The purge feed control valves 516A/B are operatively coupled to a controller 550, which can control when each stream is routed to the acid treatment vessel 132, and how much of each stream is routed to the acid treatment vessel 132. Thus, the acid treatment vessel 132 can alternate between processing a first purge stream from a first glycol reclamation vaporizer and processing a second purge stream from a second glycol reclamation vaporizer. Alternately, the acid treatment vessel 132 can concurrently process a first purge stream from a first glycol reclamation vaporizer and a second purge stream from a second glycol reclamation vaporizer. In all the above cases, the purge streams are liquid streams comprising salts, glycol and potentially water.

A portion of the material flowing in each respective pumparound line 519A and 519B can be routed to the disposal vessel 128 (FIG. 1) through respective first and second disposal control valves 530A and 530B. First and second sensors 525A and 525B, coupled to respective first and second pumparound lines 519A and 519B, can be used to determine when purge material will be disposed of or routed to treatment and recovery from the respective pumparound lines 519A and 519B. Embodiments of sensors include density and viscosity sensors.

Purge material being routed to treatment is collected into a single feed line and routed to the acid treatment vessel 132, as in the processes 100 and 300. Here, the purge material entering the acid treatment vessel 132 can be sourced from the first vaporizer 502A, the second vaporizer 502B, or both concurrently. The acid treatment process of FIG. 5 is the same as that for FIGS. 1 and 3, and the process 500 includes the divalent removal treatment of the process 300. In this case, a divalent treatment effluent control valve 514 is provided to control flow rate of effluent from the divalent removal vessel. The divalent treatment effluent control valve 514 can also be used to force all flowing material to flow through the divalent removal bypass line 324 by closing the divalent treatment effluent control valve 514.

A controller 550 controls operation of the process 500. The controller 550 is operatively coupled to the various control valves 508A, 508B, 516A, 516B, 138, 178, 316, 326, and 514 in the process 500 and adjusts operation of the various units of the process 500. The balance, cycling, and timing of flowing purge streams to the acid treatment vessel 132 is controlled by the controller 550, and can be based on the readings of the sensors 525A and 525B. Flowing purge material to the acid treatment vessel 132 can be limited by acid treatment capacity of the acid treatment vessel 132, for example by maintaining flow rate into the vessel 132 below a ceiling value. Additionally or alternately, flowing purge material to the acid treatment vessel 132 can be limited by capacity of the distillation column 148. Additionally or alternately, flowing purge material to the acid treatment vessel 132 can be limited by capacity of the divalent removal vessel 312, for example flow rate through the divalent removal vessel 312. In the event the capacity of any of the treatment units is exceeded and viscosity of either pumparound 519A or 519B is outside a tolerance range, purge material can be flowed from either pumparound to the disposal vessel 128 to hasten removal of salts or other materials that increase density or viscosity in the pumparounds 519A and B. The controller 550 can also control overall feed rates to the vaporizers 502A and B by manipulating the feed control valves 508A and B. Quantity of recycle can be manipulated by control valves 514 and 326 to ensure the feed stream 510 is not limited flowing to the vaporizers 502A and B.

While the foregoing is directed to embodiments of the present invention, other and further embodiments of the present disclosure may be devised without departing from the basic scope thereof, and the scope thereof is determined by the claims that follow.

What is claimed is:

1. A method for removing organic acid salts in monoethylene glycol recovery, comprising:
    controlling a purge stream from a vaporization separator based on a physical property indicating buildup of organic salts in monoethylene glycol that circulates through the vaporization separator, wherein the physical property comprises a viscosity or a density;
    reducing pH of the purge stream to form an acid stream;
    distilling the acid stream to form an overhead stream and a bottoms stream; and
    recycling the bottoms stream to the vaporization separator.

2. The method of claim 1, wherein distilling the acid stream comprises providing the acid stream to a distillation column having a packing, and refluxing and reboiling the distillation column.

3. The method of claim 2, wherein the acid stream is charged to the distillation column at a location between the packing and a bottom of the distillation column.

4. The method of claim 2, wherein the acid stream is charged to a feed point of the distillation column, a reboiled bottoms stream is returned to the distillation column at a return point, and the feed point is between the packing and the return point.

5. The method of claim 1, wherein reducing pH of the purge stream comprises injecting an aqueous acid solution into the purge stream to form an acid mixture and flowing the acid mixture through a vessel.

6. The method of claim 5, further comprising detecting pH of the acid stream and adjusting a flow rate of the aqueous acid solution based on the detected pH.

7. The method of claim 1, wherein the purge stream is obtained from a pumparound stream of the vaporization separator, and further comprising:
    comparing the physical property of the pumparound stream to a first threshold value indicating organic salts in the pumparound stream need treatment;
    comparing the physical property of the pumparound stream to a second threshold value indicating the organic salts in the pumparound stream do not need treatment;
    commencing the reducing pH if the physical property reaches the first threshold value; and
    discontinuing the reducing pH if the physical property reaches the second threshold value.

8. The method of claim 1, wherein recycling the bottoms stream to the vaporization separator includes routing the bottoms stream to a feed stream of the vaporization separator.

9. The method of claim 1, wherein the physical property comprises the viscosity.

10. A method for removing organic acid salts in monoethylene glycol recovery, comprising:
    detecting a physical property indicating buildup of organic salts in a pumparound stream of a glycol vaporization separator, wherein the physical property comprises a viscosity or a density;

comparing the physical property to a first threshold value indicating the organic salts in the pumparound stream need treatment;

withdrawing a purge stream from the pumparound stream if the physical property reaches the first threshold value;

reducing pH of the purge stream to form an acid stream;

distilling the acid stream to form an overhead stream and a bottoms stream; and recycling the bottoms stream to the glycol vaporization separator.

11. The method of claim 10, wherein distilling the acid stream comprises providing the acid stream to a distillation column having a packing, and refluxing and reboiling the distillation column.

12. The method of claim 11, wherein the acid stream is charged to a feed point of the distillation column, a bottoms stream of the distillation column is reboiled and returned to the distillation column at a return point, and the feed point is between the packing and the return point.

13. The method of claim 10, wherein the physical property comprises the viscosity.

14. The method of claim 10, wherein the physical property is compared to the first threshold value and to a second threshold value indicating the organic salts in the pumparound stream do not need treatment, withdrawal of the purge stream from the pumparound stream is commenced if the physical property reaches the first threshold value, and withdrawal of the purge stream is discontinued if the physical property reaches the second threshold value.

15. The method of claim 10, further comprising removing divalent species from the bottoms stream.

16. The method of claim 10, wherein reducing pH of the purge stream to form the acid stream comprises:

adding an aqueous acid treatment to the purge stream at an acid treatment rate;

mixing the purge stream with the acid treatment stream in an acid treatment vessel;

detecting a pH of the acid stream; and controlling the acid treatment rate based on the pH.

17. The method of claim 16, further comprising controlling conversion of the organic acid salts to organic acids using a pH target for the acid stream.

18. A method for removing organic acid salts in monoethylene glycol recovery, comprising:

withdrawing a purge stream from a liquid volume of a glycol vaporization separator based on a physical property of the liquid volume indicating buildup of organic salts in the liquid volume wherein the physical property comprises a viscosity or a density;

mixing an aqueous acid with the purge stream to form an acid stream at a rate of the aqueous acid that is based on a pH of the acid stream;

providing the acid stream to a packed distillation column at a location below a packing inside the packed distillation column;

distilling the acid stream to form an overhead stream and a bottoms stream; and recycling the bottoms stream to the glycol vaporization separator.

19. The method of claim 18, wherein recycling the bottoms stream to the glycol vaporization separator comprises removing divalent species from the bottoms stream.

20. The method of claim 18, wherein the physical property comprises the viscosity.

* * * * *